(12) United States Patent
Mairet et al.

(10) Patent No.: US 11,485,941 B2
(45) Date of Patent: Nov. 1, 2022

(54) SELECTIVE BIOREACTOR FOR MICROALGAE

(71) Applicants: Inria Institut Nat'l De Recherche en Informatique, Le Chesnay (FR); Centre Nat'l De La Recherche Scientifique (CNRS), Paris (FR)

(72) Inventors: Francis Mairet, Valbonne (FR); Olivier Bernard, Carros (FR); Hubert Bonnefond, Nice (FR); Antoine Sciandra, Villefranche sur mer (FR); Éric Pruvost, Nice (FR)

(73) Assignees: Inria Institut National De Recherche En Informatique Et En Automatique; Centre National De La Recherche Scientifique (C.N.R.S.)

( * ) Notice: Subject to any disclaimer, the term of this patent is extended or adjusted under 35 U.S.C. 154(b) by 713 days.

(21) Appl. No.: 16/091,100

(22) PCT Filed: Apr. 3, 2017

(86) PCT No.: PCT/FR2017/050765
§ 371 (c)(1),
(2) Date: Oct. 3, 2018

(87) PCT Pub. No.: WO2017/174907
PCT Pub. Date: Oct. 12, 2017

(65) Prior Publication Data
US 2019/0119614 A1 Apr. 25, 2019

(30) Foreign Application Priority Data
Apr. 4, 2016 (FR) ...................... 1652933

(51) Int. Cl.
*C12M 1/00* (2006.01)
*C12M 1/42* (2006.01)
*C12N 5/00* (2006.01)

(52) U.S. Cl.
CPC ............ *C12M 21/02* (2013.01); *C12M 35/02* (2013.01); *C12M 41/06* (2013.01); *C12N 5/0018* (2013.01)

(58) Field of Classification Search
CPC ...... C12M 21/02; C12M 35/02; C12M 41/06; C12N 5/0018
See application file for complete search history.

(56) References Cited

U.S. PATENT DOCUMENTS

| 5,882,849 A | 3/1999 | Leonard et al. |
| 9,131,645 B2 * | 9/2015 | Karpinski ............. A01G 7/045 |

(Continued)

FOREIGN PATENT DOCUMENTS

KR 1020040059182 A 7/2004

*Primary Examiner* — William H. Beisner
*Assistant Examiner* — Danielle B Henkel
(74) *Attorney, Agent, or Firm* — Maynard Cooper & Gale, P. C.; Brian T. Sattizahn

(57) ABSTRACT

The invention relates to a bioreactor including: a light source (200); a light sensor (300) facing said light source; a vat (100) that is placed between the light source (200) and the light sensor (300), said vat being intended to receive a culture medium comprising a cellular culture of photosynthetic microorganisms; a controller (400) connected to the light sensor (300) in order to control the vat (100) to obtain a chosen cellular-culture concentration (xi) in the culture medium during a working period, said light source (200) being capable of emitting incident light (L) of an input light intensity (Iin) in the direction of the vat (100), and the light sensor (300) being capable of measuring an output light intensity (Iout) and of transmitting data relating to this intensity (Iout) to the controller for the control of the vat;

(Continued)

and a system (500) for controlling the light source (200), this system being arranged to adjust, during a period shorter than or equal to said working period, the input light intensity (Iin) to a setpoint value allowing a cellular stress to be induced in certain at least of said photosynthetic microorganisms.

18 Claims, 4 Drawing Sheets

(56) References Cited

U.S. PATENT DOCUMENTS

| | | | |
|---|---|---|---|
| 2005/0064577 A1* | 3/2005 | Berzin | B01D 53/85 |
| | | | 435/266 |
| 2007/0231886 A1 | 10/2007 | Kahlert et al. | |
| 2009/0047722 A1* | 2/2009 | Wilkerson | C12M 31/10 |
| | | | 435/173.7 |
| 2009/0148931 A1* | 6/2009 | Wilkerson | F24S 23/12 |
| | | | 435/286.1 |
| 2009/0291485 A1* | 11/2009 | Shigematsu | C12N 1/10 |
| | | | 362/249.14 |
| 2010/0255458 A1* | 10/2010 | Kinkaid | C12N 1/20 |
| | | | 435/257.1 |
| 2013/0239461 A1* | 9/2013 | Kramer | C12M 41/48 |
| | | | 435/292.1 |
| 2013/0309762 A1* | 11/2013 | Sim | C12M 21/02 |
| | | | 435/292.1 |
| 2014/0356902 A1 | 12/2014 | Weissman et al. | |
| 2015/0087014 A1* | 3/2015 | Weissman | C12Q 1/04 |
| | | | 435/288.7 |
| 2019/0284516 A1* | 9/2019 | Bernard | C12M 21/02 |

* cited by examiner

SELECTIVE BIOREACTOR FOR MICROALGAE

The present invention relates to a bioreactor for selecting microalgal strains. The invention also relates to a process for selecting microalgal strains.

Both prokaryotic and eukaryotic photosynthetic microorganisms exist, which are grouped together under the term "microalgae". Prokaryotic photosynthetic microorganisms are represented by cyanobacteria (sometimes referred to as "blue-green algae"). Eukaryotic photosynthetic microorganisms are represented by a multitude of classes, among which mention may be made of Chlorophyceae, diatoms, Chrysophyceae, Coccolithophyceae, Euglenophyceae and Rhodophyceae. Generally speaking, the size of a microalgal cell is between 1 μm and 100 μm.

Current estimates suggest that there are more than a million species of microalgae, of which several tens of thousands of species are catalogued. Microalgae are ubiquitous and they are found equally in fresh water, brackish water and sea water.

Microalgae production is a fast-growing sector. This is because microalgae synthesize numerous products of different natures, among which mention may be made of proteins, antioxidants, pigments, and the long-chain polyunsaturated fatty acids DHA (docosahexaenoic acid) and EPA (eicosapentaenoic acid).

Thus, microalgae have applications in several technological fields and especially in the cosmetics industry, the pharmaceutical industry, aquaculture, functional foods or food supplements.

Microalgae are also used in the production of bioenergy. Microalgae have the ability to capture light energy in order to fix and metabolize inorganic carbon from carbon dioxide ($CO_2$) in energy molecules. The coupling of microalgae with $CO_2$ and the fact that microalgae are often rich in sugars or in oils means that microalgae are of great benefit in the production of biofuels. This coupling is also the source of the purifying properties possessed by microalgae.

Microalgae are photosynthetic species. The cells of microalgae need light to proliferate. Microalgae may be cultured using natural light (sunlight) or artificial light. There are open culture systems of the culture pond type (also referred to as "raceway" pond), and closed culture systems such as batch bioreactors, fed-batch bioreactors or continuous bioreactors.

Generally speaking, all the culture systems have a tank intended to receive a culture medium comprising nutrients. The microalgae are dispersed in this culture medium and receive light. Continuous bioreactors have the advantage of having an input and an output for culture medium, associated with a controller. The controller makes it possible to control the tank continuously to a chosen microalgae concentration in the culture medium during a working period.

In open or closed culture systems, the light is predominantly absorbed by the cells close to the light source. When the microalgae density is high, a large portion of the light is not able to deeply penetrate the tank. Consequently, the microalgae at depth in the tanks are located in darkness and cannot correctly proliferate.

The culture systems have a problem of overexposure to light of the cells close to the light source and a problem of underexposure of the cells located at depth in the culture medium. This light gradient within the culture systems limits the production of microalgae.

The prior art proposes an approach consisting in genetically modifying microalgae. This involves reducing the size or the number of the light-harvesting complexes (chlorophyll molecules) and/or modifying the ratios between the different pigments (especially chlorophyll a, chlorophyll b, chlorophyll c, carotenoids and other pigments) of the microalgae, in order to make them more transparent.

Document WO 2014/089533 discloses mutant microalgae having reduced light-harvesting complexes.

In this approach, each microalgal cell captures a smaller amounts of light, enabling the light to deeply penetrate the tanks. The cells located in the regions furthest from the light source are therefore less shaded. However, this approach requires complex and costly methods of genetic engineering or of mutation-selection, such as chemical mutagenesis or treatment by ultraviolet or gamma irradiation. Moreover, the culture systems only comprise a single type of mutant: these are microalgal monocultures. Monocultures are less robust, especially when confronted with industrial production conditions. The prior art also proposes an approach consisting in selecting microalgal strains that are rich in components used in the production of biofuels.

Document WO 2013/012329 discloses a process for selecting microalgae having an increased capacity for storing components of use for producing biofuels.

In this approach, a culture of different microalgal strains is subjected to a nutritional stress. Only the strains capable of storing a high concentration of nutrients survive this stress. The strains are harvested and cultured in the culture systems described above. The problems associated with the light gradient remain.

The present invention will improve the situation.

To this end, the invention will introduce a bioreactor comprising a light source, a light sensor facing said light source and a tank arranged between the light source and the light sensor intended to receive a culture medium comprising a cell culture of photosynthetic microorganisms, a controller connected to the light sensor to control the tank to a chosen cell culture concentration in the culture medium during a working period, said light source being capable of emitting an incident light with an input light intensity in the direction of the tank, and the light sensor being capable of measuring an output light intensity and of transmitting data relating to this intensity to the controller for controlling the tank, and a system for controlling the light source arranged to set, for a period less than or equal to said working period, the input light intensity to a setpoint value enabling to induce cellular stress in at least some of said photosynthetic microorganisms.

The setpoint value may be greater than or equal to 500 μmol quanta $m^{-2}$ $s^{-1}$. It is preferably greater than or equal to 800 μmol quanta $m^{-2}$ $s^{-1}$. The chosen cell culture concentration ($x_i$) in the culture medium may be between 0.001 g/l and 10 g/l.

According to one embodiment, the chosen cell culture concentration ($x_i$) in the culture medium is between 0.001 g/l and 0.1 g/l, preferably between 0.05 g/l and 0.1 g/l.

The control system may be arranged to set said light to an input light intensity ($I_{in}$) at a resting value lower than the setpoint value, and to switch between the resting value and the setpoint value during the working period. The control system may be arranged to fix a first irradiation period for which the light is set to the input light intensity ($I_{in}$) at the resting value and a second irradiation period for which the light is set to the setpoint value, the first irradiation period being greater than the second irradiation period, and to apply a succession of the first and second irradiation periods. The first and second irradiation periods may be fixed such that the mean value of the input light intensity ($I_{in}$) during the working period, calculated from the resting value and the setpoint value, is less than or equal to a third of said setpoint value. In one embodiment, the first irradiation period is at least three times greater than the second irradiation period. The control system may be arranged to fix a plurality of first and second irradiation periods during which the light is set to an input light intensity ($I_{in}$) at the resting value during each first irradiation period and the light is set to an input light intensity ($I_{in}$) at the setpoint value during each second irradiation period. The control system may be arranged to fix the setpoint value at each second irradiation period.

In another embodiment, the chosen cell culture concentration ($x_i$) in the culture medium is between 0.1 g/l and 10 g/l, preferably between 1 g/l and 10 g/l. In this embodiment, the control system may be arranged to maintain the input light intensity ($I_{in}$) at the setpoint value, such that the output light intensity ($I_{out}$) is substantially constant for a period less than or equal to the working period.

The invention also relates to a process for selecting photosynthetic microorganisms, comprising the following steps:
1. providing a bioreactor comprising a light source, and a tank arranged facing the light source intended to receive a culture medium comprising a cell culture of photosynthetic microorganisms, said light source being capable of emitting a light with an input light intensity $I_{in}$ in the direction of the tank,
2. filling the tank with a culture medium;
3. inoculating the culture medium with a cell culture composed of photosynthetic microorganisms;
4. controlling the tank for a working period to a chosen cell culture concentration $x_i$ in the culture medium;
5. setting the input light intensity $I_{in}$ to a setpoint value enabling to induce cellular stress in at least some of said photosynthetic microorganisms;
6. maintaining the input light intensity $I_{in}$ at the setpoint value for a period less than or equal to said working period, so as to cause cellular degradation of at least a portion of said photosynthetic microorganisms and thereby select the photosynthetic microorganisms having increased resistance to photoinhibition; and
7. harvesting the photosynthetic microorganisms having increased resistance to photoinhibition from said culture medium.

The harvesting at step 7. may be carried out when the culture medium comprises a cell culture of photosynthetic microorganisms consisting of more than 75%, preferentially of more than 90%, even more preferentially substantially to 100%, of microorganisms having increased resistance to photoinhibition.

In one embodiment, the process implements successive repetition of steps 5. and 6. until a cell culture of photosynthetic microorganisms consisting of microorganisms having increased resistance to photoinhibition is obtained.

Step 6. of the process of the invention may comprise the following sub-steps:
6a. setting the light to an input light intensity ($I_{in}$) at a resting value lower than the setpoint value, for a period less than said working period;
6b. maintaining the input light intensity ($I_{in}$) at the resting value for a period less than said working period; and
6c. successively switching between the resting value and setpoint value during the working period.

The process of the invention may also comprise the following steps:
8. inoculating a culture medium with the photosynthetic microorganisms harvested in step 7. in a bioreactor; and
9. controlling the bioreactor of step 8. for production of biomass formed of said photosynthetic microorganisms.

The bioreactor used in the process may also comprise a light sensor arranged opposite the light source relative to the tank, the light sensor being capable of measuring an output light intensity ($I_{out}$). In this embodiment, the process also comprises the step 4a. of measuring the output light intensity ($I_{out}$). In this embodiment, the input light intensity ($I_{in}$) at step 5. is set as a function of the output light intensity ($I_{out}$) measured in step 4a.

Other features and advantages of the invention will become apparent upon reading the following detailed description and the appended drawings, in which.

The drawings and the description hereinafter essentially contain elements that are certain in nature. They form an integral part of the description, and may therefore not only serve for improved understanding of the present invention, but also contribute to the definition thereof where appropriate.

For good production of microalgae (or microalgal biomass), it is appropriate to culture them in a culture medium rich in nutrients (nitrogen, phosphorus, sulfur, trace elements, vitamins) and to provide sufficient light. The presence of nutrients is necessary to enable the microalgae to convert light energy by metabolizing $CO_2$. This conversion results in the production of oxygen and the increase in biomass by the proliferation of the microalgae (multiplication by cell division).

Conventionally, a light source is used that is capable of emitting light at a wavelength strongly absorbed by the microalgae, in order to obtain a high rate of growth.

The publications *Light requirements in microalgal photobioreactors: an overview of biophotonic aspects*—Carvalho et al., Appl Microbiology and Biotechnology, 2011, vol. 89, no. 5: 1275-1288 and *Light emitting diodes (LEDs) applied to microalgal production*—Schulze et al., Trends in Biotechnology, 2014, vol. 32, no. 8: 422-430 describe the use of light in systems for culturing microalgae in order to obtain good cell growth.

In a bioreactor, the microalgae may receive an excess of photons which may lead to a decrease in photosynthetic efficiency. This corresponds to a dissipation of energy, referred to as non-photochemical quenching. The phenomenon of non-photochemical quenching is especially described in the article *Non-Photochemical Quenching. A Response to Excess Light Energy*—Müller et al., Plant Physiol, 2001, vol. 125, no. 4: 1558-1566. Moreover, the excess photon absorption may cause degradation of the photosynthetic apparatus which reduces, or even inhibits, proliferation of the microalgae. This phenomenon is referred to as photoinhibition.

Figure 1:
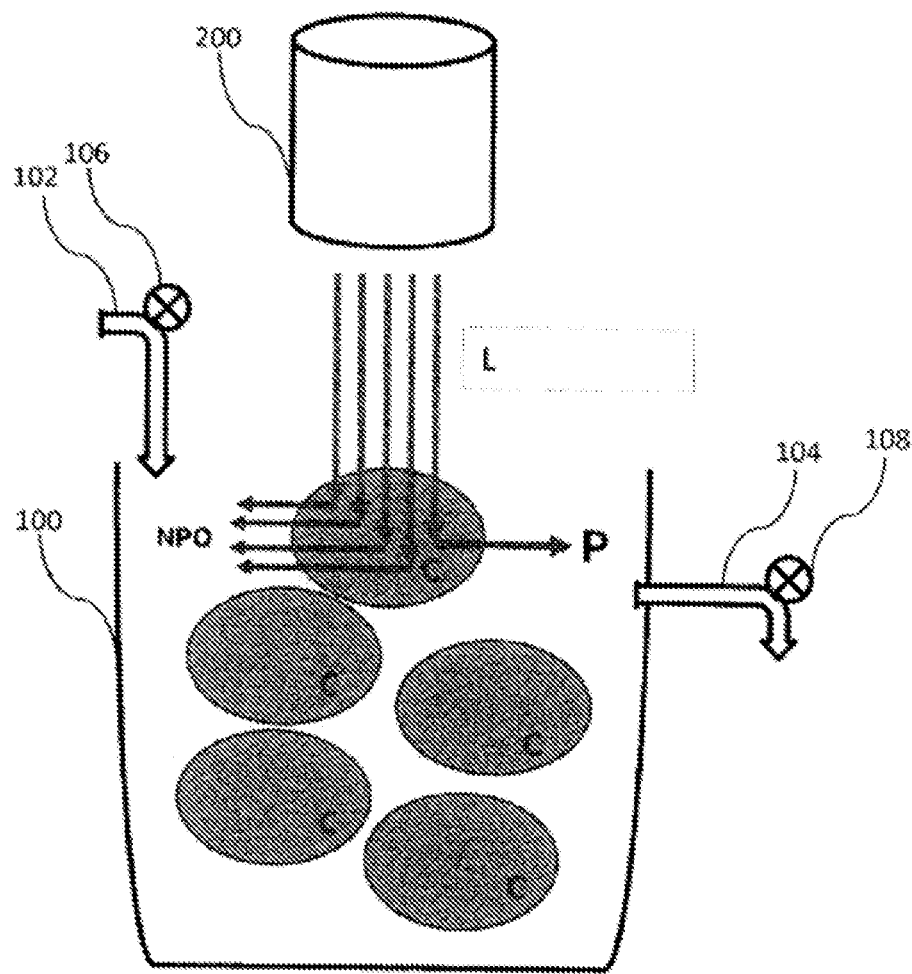
FIG. 1 shows a diagram for production of microalgae in a culture system.

FIG. 1 shows a diagram for production of microalgal biomass in a continuous bioreactor.

The bioreactor comprises a tank 100 able to receive a culture medium comprising microalgae. The microalgae are dispersed in the culture medium or are in the form of a biofilm. The microalgae consist of cells C of photosynthetic microorganisms. The bioreactor comprises an input 102 and an output 104 respectively associated with a flow regulating device. Thus, the input 102 and the output 104 are respectively associated with a first valve (or pump) 106 and a second valve (or pump) 108 in order to open and close the input 102 and the output 104. The input 102 and the first valve 106 make it possible to control the supply of fresh culture medium in the tank 100. The output 104 and the second valve 108 make it possible to control the evacuation of the culture medium and, where appropriate, at least some of the cells C. The input and the output make it possible to continuously control the bioreactor for a production P of microalgal biomass.

Generally speaking, the control of the production of biomass in a continuous culture system relies on management of the cell growth of the microalgal culture. The concentration x [g/l] of microalgae in the culture medium changes as a function of the specific growth rate $\mu(x)$ [h$^{-1}$] and of the level of dilution D [h$^{-1}$] of the culture medium. The level of dilution D is defined by the input flow rate (l/h) divided by the volume (l) of the culture medium.

The concentration x [g/l] of microalgae in the culture medium changes over time. For a given strain of microalgae this change may be expressed by the following formula F1:

$$\dot{x} = \mu x - Dx \quad [F1]$$

Consequently, for the production of biomass in the tank 100 of the bioreactor (at constant volume):

- If $\mu(x) > D$: the cells multiply (by cell division) more rapidly than they are evacuated; their number and therefore their concentration (biomass) will increase.
- If $\mu(x) < D$: the cells multiply (by cell division) less rapidly than they are evacuated; their number and therefore their concentration (biomass) will decrease.
- If $\mu(x) = D$: the number of cells remains constant over time. The number of cells evacuated with the culture medium from the tank is equal to the number of cells obtained by multiplication thereof in the culture medium within the tank. The concentration is stable.

The bioreactor comprises a light source 200. The light source 200 is able to emit an incident light L. The light L is typically chosen to cover the entire solar spectrum including blue light (preferably from 430 nm to 470 nm) and red light (preferably from 650 nm to 700 nm). These wavelength ranges enable a good growth rate of the microalgae since they are greatly absorbed by the latter.

The phenomena of optics, absorbance and metabolization of photons in a bioreactor tank are described in detail in the works *Microalgal biotechnology: potential and production*, C. Posten and C. Walter, de Gruyter, 2012 and *Handbook of Microalgal Culture: Applied Phycology and Biotechnology*, 2$^{nd}$ edition, A. Richmond and Q. Hu, Wiley-Blackwell, 2013.

The incident light L essentially illuminates the microalgal cells close to the light source 200. These microalgae receive the majority of the photons emitted by the light source 200. This induces the phenomenon of non-photochemical quenching (NPQ) and also photoinhibition. The microalgal cells located at depth in the tank 100 are not illuminated, or virtually not illuminated, which prevents them from proliferating. This is particularly true with high cell density, that is to say when the concentration of microalgae in the tank 100 is high (for example between 1 g/l and 10 g/l).

The resulting production P of biomass is unsatisfactory. In order to deal with this problem, some culture systems of the prior art use improved mixing tools promoting circulation of the microalgae within the tank. In this way, all the cells are exposed to the light.

However, the use of these tools presents a significant expenditure of energy and the existing problems associated with photoinhibition and light gradient are not solved.

The present invention proposes a radically different approach. Thus, instead of attempting to avoid the effects of photoinhibition, the invention proposes exploiting this.

The applicant discovered, not unsurprisingly, that, in a culture system, photoinhibition makes it possible to select microalgae that are suitable for industrial exploitation. The system may be controlled continuously or semi-continuously, as fed-batch type.

Some species of microalgae are capable of adjusting their content of photoreceptive pigments as a function of the light received. This phenomenon is referred to as photoacclimation. The microalgae exposed to a high light intensity acclimatize to this high light intensity and become more translucent. The microalgae become more translucent especially by decreasing the presence of photoreceptor pigments within the cells. The microalgal cells thereby become more resistant to photoinhibition. For example, the species *Chlorella sorokiniana* is known, which has increased resistance to photoinhibition; cf. *Chlorella sorokiniana UTEX 2805, a heat and intense, sunlight-tolerant microalga with potential for removing ammonium from wastewater*—Bashan, L. E., Trejo, A., Huss, V. A., Hernandez, J. P., & Bashan, Y., Bioresource Technology, 99(11), 4980-4989, 2008. Generally speaking, resistance to high light intensities may originate from the ability of some species to decrease their pigment content. In culture systems, these translucent microalgae allow a large portion of the incident light to pass to the depth of the tank. The problem associated with the light gradient in the tank is reduced or even solved.

However, there are currently few known species with increased resistance to photoinhibition.

Moreover, when these species of microalgae are exposed to a low light intensity, they acclimatize to this low light intensity and become more opaque. Thus, in high-density culture systems, for example a microalgae concentration of greater than 0.1 g/l, the mean light intensity at depth in the tank is low. Consequently, the microalgae lose the benefit of their transparency acquired during exposure to a high light intensity.

One aim of the invention is therefore especially to generate novel microalgal strains which, even with weak light (at low light intensity), have a low pigment content and/or which undergo modification of the pigmentary apparatus. Greater biomasses may then be obtained in the culture systems. Generally speaking, light stress results in adaptation of microalgal cells. This adaptation is especially reflected in genetic mutations within the microalgal cells. In other words, the natural genetic mutations induced by the light stress lead to mechanisms of genetic adaptation. The genetic mutations are capable of being transmitted from a cell to its daughter cells, and therefore of being transmitted from generation to generation. A genetic mutation may for example result in a reduction in the content of photoreceptors (such as chlorophyll) in the microalgal cells. It may also lead to an increase in the rate of recycling of pigments, and hence the active production/degradation thereof, or else to a modification of the ratios of the different pigments in the cell. In this way, the microalgae become more translucent and allow a large portion of the incident light to pass, which reduces or solves the problem associated with the light gradient in tanks of culture systems.

Figure 2:
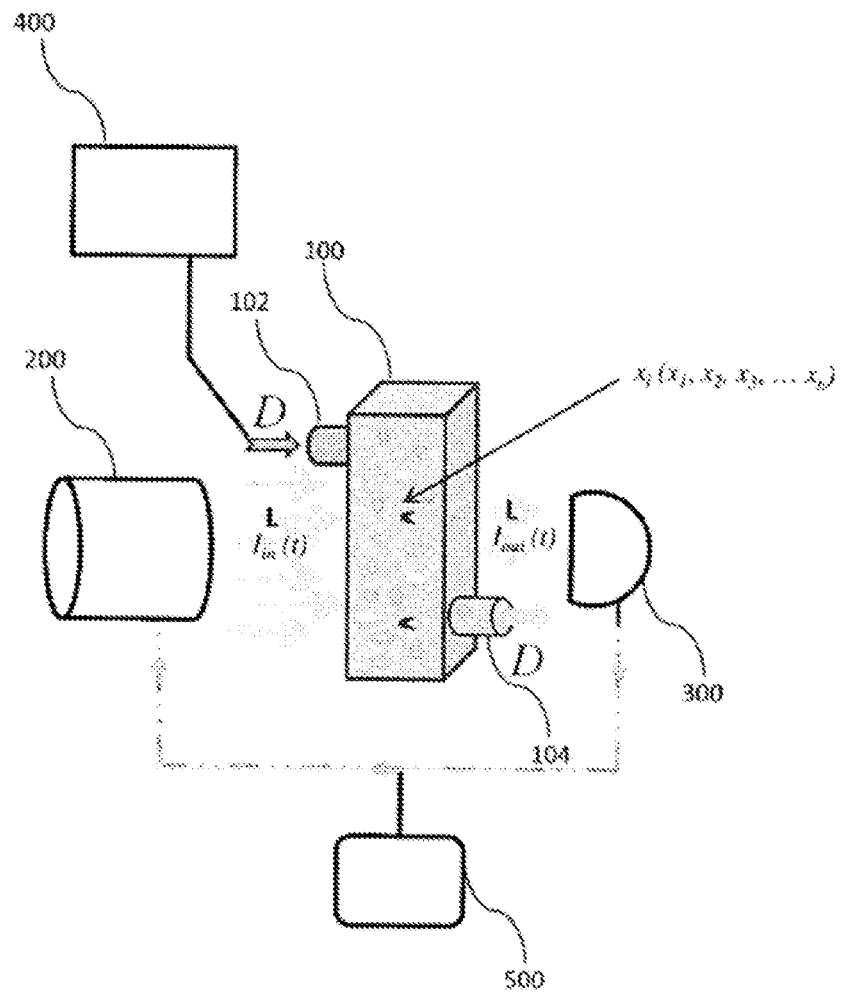
FIG. 2 shows a schematic diagram of the bioreactor of the invention during a working period.

FIG. 2 shows a schematic diagram of the bioreactor of the invention during a working period.

The bioreactor comprises a tank 100 with a culture medium. The culture medium comprises a dispersion of a cell culture of photosynthetic microorganisms. The cell culture comprises n different strains of photosynthetic microorganisms ("different strains" is intended to mean different genotypes or phenotypes of one or more species of microalgae) of respective concentrations $x_1$, $x_2$, $x_3$ ... $x_n$. The different strains of photosynthetic microorganisms are more or less resistant to photoinhibition. The tank 100 has means for mixing the culture medium.

The bioreactor also comprises an input 102 and an output 104. The input 102 makes it possible to supply fresh culture medium to the tank 100. The output 104 makes it possible to evacuate culture medium and microalgae from the tank 100.

The input 102 and the output 104 are associated with a controller 400. The controller 400 makes it possible to continuously control the tank 100 for a working period. The working period varies depending on the microalgal strains present in the culture medium. The working period lasts preferentially at least 1 month (without an upper time limit), which generally corresponds to at least 20 generations of microalgae (that is to say 20 successive cell divisions). According to the invention, the working period is greater than the time required for one microalgal cell cycle. In one embodiment, the working period extends from 6 to 12 months.

The controller 400 continuously controls the tank 100 to a level of dilution D. For this purpose, the controller 400 comprises one or more photoelectric cells to measure the optical density of the combined culture medium/microalgae within the tank 100. In this way, the controller may maintain the cell culture concentration $\Sigma x_i$ in the culture medium between 0.001 g/l and 10 g/l, preferably between 0.05 g/l and 0.1 g/l or between 0.1 and 5 g/l, during the working period and adapt the level of dilution D by supplying and evacuating culture medium. In other words, the total concentration consisting of the respective concentrations $x_1$, $x_2$, $x_3$ ... $x_n$ of the different microalgal strains is between 0.05 g/l and 0.1 g/l during the working period. This concentration enables good diffusion of light within the tank 100.

The bioreactor comprises a light source 200 which emits incident light L with a sufficiently high input light intensity $I_{in}$ to pass through the tank 100 filled with the culture medium comprising the dispersion of microalgae. In the present embodiment, the light source 200 is capable of emitting an input light intensity $I_{in}$ which may extend up to 5000 µmol quanta m$^{-2}$ s$^{-1}$.

The bioreactor also comprises a light sensor 300 arranged facing said light source for measuring the light intensity of the light L that has passed through the tank 100. The intensity of the light that has passed through the tank 100 filled with the culture medium comprising the dispersion of microalgae is referred to as the output light intensity $I_{out}$. The light sensor 300 measures the output light intensity $I_{out}$ and transmits the data to the controller 400 for controlling the tank. Transmission may be direct or indirect, via a control system 500 described below.

A control system 500 is connected to the light source 200 and makes it possible to maintain the input light intensity $I_{in}$ constant, to increase it or to decrease it. The control system 500 is arranged to set the input light intensity $I_{in}$ to a setpoint value. In the embodiment described here, the control system 500 is also connected to the light sensor 300. Connection to the light sensor 300 enables the control system 500 to receive data relating to the output light intensity $I_{out}$ measured by the sensor 300. The control system 500 may thus transmit this data to the controller 400 in order for the latter to be able to continuously control the tank to the setpoint concentration.

The input light intensity), and the output light intensity $I_{out}$ may vary during the working period. Thus, the control system 500 is arranged to set the input light intensity $I_{in}$ to the setpoint value for a period less than or equal to the working period.

The time-dependent relationship between the input light intensity $I_{in}$ and the output light intensity $I_{out}$ is defined by the following formula F2:

$$I_{out}(t) = I_{in}(t)\exp\left(-\sum_{i=1}^{n} a_i x_i P\right) \quad [F2]$$

in which $a_i$ is the attenuation coefficient of the microalgae (that is to say the amount of light absorbed by the microalgae); $x_i$ is the concentration of the microalgae; and P is the distance between the light source 200 and the light sensor 300.

By setting the input light intensity $I_{in}$ the control system 500 can also control the output light intensity $I_{out}$.

According to the invention, the control system 500 is arranged to set the input light intensity $I_{in}$ to a setpoint value for a period less than or equal to said working period, in order to induce cellular stress in at least some of the microalgae present in the cell culture. In one preferential embodiment, the control system 500 is arranged to set the input light intensity $I_{in}$ to a setpoint value greater than or equal to 500 µmol quanta m$^{-2}$ s$^{-1}$.

The control system 500 is arranged to receive data relating to the setpoint value. The setpoint value may especially vary as a function of one or more species of photosynthetic microorganisms present in the tank 100. The setpoint value may also vary as a function of the cell culture concentration $x_i$ in the culture medium.

The setpoint value may change during the working period. In one embodiment, the working period is composed of a succession of distinct predefined intervals of time. Each interval is less than the working period. In this embodiment, the control system 500 may set the input light intensity ($I_{in}$) to the setpoint value during each of said time intervals. The setpoint value may be fixed specifically for each interval. The setpoint value may therefore be different from one interval to another. In a preferential embodiment, the setpoint value increases from one interval to the next, for example in stages of 100 to 200 µma quanta m$^{-2}$ s$^{-1}$. The intervals may be of the same duration or of different durations.

In another embodiment, the control system 500 may control the input light intensity $I_{in}$ as a function of data relating to the output light intensity $I_{out}$ measured by the sensor 300. In this embodiment, the control system 500 may be arranged to receive data from the sensor 300, then to adjust the input light intensity $I_{in}$ to the desired setpoint value as a function of the data received.

The control system 500 may be arranged to maintain the input light intensity ($I_{in}$) at a setpoint value such that the output light intensity ($I_{out}$) is substantially constant for a period less than or equal to the working period.

In one embodiment, the output light intensity ($I_{out}$) may be substantially constant during the whole of the working period. In this embodiment, the control system 500 therefore sets the input light intensity ($I_{in}$) to the setpoint value and maintains it during the whole of the working period. The light intensity ($I_{in}$) is for example adjusted as a function of the cell culture concentration $x_i$ in the culture medium. The more the concentration increases, the more the light intensity ($I_{in}$) increases in order to maintain a constant output light intensity ($I_{out}$).

In another embodiment, the output light intensity ($I_{out}$) is substantially constant for a predefined period less than the working period. In this embodiment, the control system 500 sets the input light intensity ($I_{in}$) to the setpoint value during this predefined period (for example also as a function of the change in the cell concentration in the medium).

In yet another embodiment, the output light intensity ($I_{out}$) is substantially constant during distinct predefined intervals of time, each predefined interval of time being less than the working period. In this embodiment, the control system 500 sets the input light intensity ($I_{in}$) to the setpoint value during each of said time intervals. The setpoint value may be fixed specifically for each of the intervals. The setpoint value may therefore be different from one interval to another. In one preferential embodiment, the working period is composed of a succession of intervals. The setpoint value changes throughout the whole of said working period and increases in stages of 100 to 200 µmol quanta $m^{-2}$ $s^{-1}$ for each interval. The intervals may be of the same duration or of different durations.

Inducing cellular stress in certain microalgae has at least two consequences:
- a first consequence is that some microalgae affected by cellular stress may be subject to the phenomenon of photoinhibition. Some key proteins of the photosynthetic apparatus are damaged and growth slows. The phenomenon may go as far as stopping the cell cycle; they stop dividing or undergo cell death;
- a second consequence is that other microalgae affected by cellular stress may adapt genetically (especially by nucleotide point mutations). They are less damaged and the cell cycle of these microalgae is not stopped; they have increased resistance to photoinhibition. As explained above, this resistance is associated with the fact that these microalgae become more transparent (low pigment content).

The controller 400 controls the tank 100 continuously to a level of dilution D during the working period that is much greater than the time required for one microalgal cell cycle.

Consequently, the tank 100 is gradually emptied of the microalgal cells affected by the first consequence. This is because the cells affected stop dividing, and their specific growth then becomes lower than the rate ($\mu(x)<D$).

On the other hand, the microalgal cells affected by the second consequence remain represented throughout the whole working period in the tank 100 because their specific growth ($\mu(x)$) is not, or is only slightly, affected.

Moreover, the cells of the microalgal strains having increased resistance to photoinhibition and which were already present in the cell culture also remain represented in the tank 100 throughout the whole working period. Their specific growth ($\mu(x)$) is not, or is only slightly, affected.

Preferably, the working period is greater than the time required for at least 20 cell cycles, preferably 100 cell cycles, of each initial microalgal cell present in the culture medium. In the present embodiment, the working period is 20 days and preferably 100 days.

In one embodiment, the control system 500 is arranged to set the light to an input light intensity at a resting value $I_{in0}$. Thus, the control system 500 may successively switch between a light intensity set at the resting value and a light intensity set at the setpoint value.

In one embodiment, the resting value is less than or equal to 100 µmol quanta $m^{-2}$ $s^{-1}$. Thus, the control system 500 may successively switch during the working period between incident light with an intensity $I_{in0}$ less than or equal to 100 µmol quanta $m^{-2}$ $s^{-1}$ (referred to as "low-intensity") and an intensity $I_{in1}$ greater than or equal to 500 µmol quanta $m^{-2}$ $s^{-1}$ (referred to as "high-intensity"). The switching time T is less than the working period (typically between 30 minutes and 1 hour). Thus, the control system 500 may switch between the light with input light intensity $I_{in1}$ (referred to as "high-intensity") for a fraction p of the period, inducing cellular stress, and the low-intensity light $I_{in0}$, for a fraction (1−p) of the period. The fraction p is typically less than or equal to 0.1. Thus, the control system 500 may fix a first period of irradiation at low intensity for a duration (1−p)·T and a second period of irradiation at high intensity for a duration p·T.

The mean light received by the cells for a low-density culture is therefore $$\bar{I}_{in} = p \cdot I_{in1} + (1-p) \cdot I_{in0}$$

The parameters above are chosen and/or adapted depending on the microalgal species. The choice is made such that firstly, during the high-intensity phases, the cellular stress of at least some of the microalgae present in the cell culture is induced, and that secondly the cells acclimatize to a low mean light $\bar{I}_{in}$, reflecting high-density culture conditions; they will thus be under conditions for the maximum synthesis of pigments.

According to one embodiment of the invention, the irradiation periods are fixed such that the mean value of the input light intensity ($I_{in}$) during the working period, calculated from the resting value and the setpoint value, is less than or equal to a third of said setpoint value. In a preferential embodiment, the first irradiation period is at least three times greater than the second irradiation period. A plurality of first and second irradiation periods may be defined. During the plurality of first and second irradiation periods, the light may be set to an input light intensity ($I_{in}$) at the resting value during each first irradiation period and the light is set to an input light intensity ($I_{in}$) at the setpoint value during each second irradiation period. The setpoint value may be fixed for each second irradiation period. In this way, the setpoint value may vary throughout the whole of the working period.

In another embodiment, the control system 500 sets the input light intensity 4, such that the output light intensity $I_{out}$ is substantially constant at a sufficiently high value to induce photoinhibition. For example, this value may be greater than or equal to 500 µmol quanta $m^{-2}$ $s^{-1}$. In this embodiment, throughout the whole of the working period, the microalgal cells close to the light source 200 are subjected to high intensity, that is to say subject to light with an intensity set to a setpoint value enabling to induce cellular stress in the microalgae. At least a portion of the microalgal cells of the cell culture is therefore constantly subjected to cellular stress. This embodiment is particularly advantageous for identifying strains having increased resistance to photoinhibition and which were initially contained in the initial diversity of the population of microalgae, or else which have appeared by a process of genetic mutation during the working period. In one embodiment, the working period is 6 months, the output light intensity $I_{out}$ is 1000 µmol quanta $m^{-2}$ $s^{-1}$; and the level of dilution is 0.3 $d^{-1}$.

As explained above, in this embodiment the setpoint value may change in stages over the working period.

Figure 3:
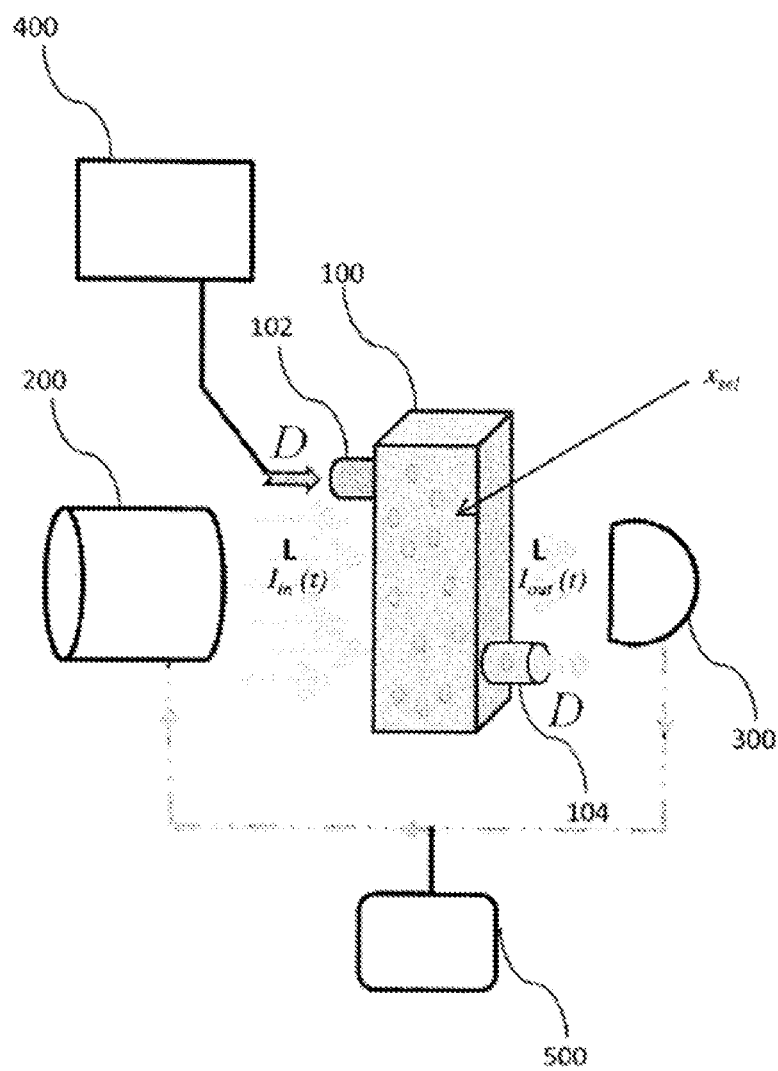
FIG. 3 shows a schematic diagram of the bioreactor of FIG. 2 at the end of the working period.

FIG. 3 shows a schematic diagram of the bioreactor of FIG. 2 of the invention at the end of the working period.

The culture medium in the tank 100 initially comprised a dispersion of a cell culture of microalgae comprising natural variability of individuals that are more or less resistant to photoinhibition at respective concentrations $x_1, x_2, x_3 \ldots x_n$, the different microalgal strains being more or less resistant to photoinhibition (cf. FIG. 2).

At the end of the working period, the tank 100 comprises a dispersion of a cell culture of microalgae having a concentration $x_{sel}$ of one or more microalgal strains each having increased resistance to photoinhibition. The controller is arranged to adapt the level of dilution D during the working period. In one embodiment, the concentration $x_{sel}$ is substantially identical to that of the initial concentration $x_i$, namely between 0.05 g/l and 0.1 g/l. The controller 400 makes it possible to close the input 102 and the output 104 in order to harvest the microalgal strain(s) having increased resistance to photoinhibition. The harvesting may especially be carried out by sampling from the tank 100.

The bioreactor of the invention therefore makes it possible to obtain photosynthetic microorganisms having increased resistance to photoinhibition. Increased resistance is intended to mean a small decrease in the rate of growth (of the order of −25%) for a light intensity that is two times greater than the optimal intensity for growth.

The greater the light intensity, the stricter the selection. Advantageously, the level of stress is increased gradually during the working period. This may be carried out by increasing the mean light intensity during the working period, especially by increasing the setpoint intensity as the working period advances.

The operation of the bioreactor of the invention is independent of the number of microalgal strains present in the culture medium. In other embodiments, this may be a monoculture, namely a culture comprising just one microalgal strain. In these embodiments, the microalgal cells may be adapted or transformed by the bioreactor of the invention, for example by point mutations in their nucleotide sequences.

EXAMPLE

The example uses a bioreactor having a plurality of probes and sensors. The bioreactor especially comprises a probe for measuring the pH and temperature of the culture medium, a PAR sensor for measuring the photosynthetic radiation, a turbidity sensor for measuring the optical density at 750 nm, a fluorescent oxygen sensor for measuring the respiration rate and a light attenuation sensor made of a photodiode that captures light $I_{in}$ or an additional source such as an LED or a laser beam.

The bioreactor also has a level sensor of the 600 nm laser barrier type. The bioreactor is coupled to a computer-controlled marine environment simulator [*Simulateur d'Environnement Marin Piloté par Ordinateur (SEMPO)*] making it possible to experimentally reproduce a marine environment that promotes microalgal proliferation, cf. The effects of a controlled fluctuating nutrient environment on continuous cultures of phytoplankton monitored by computers Bernard, O., Malara, G., & Sciandra, A., Journal of Experimental Marine Biology and Ecology, 197(2), 263-278, 1996, and *An automatic device for in vivo absorption spectra acquisition and chlorophyll estimation in phytoplankton cultures*—Le Floc'h, E., Malara, G., & Sciandra, A., Journal of applied phycology, 14(6), 435-444, 2002. The bioreactor is also coupled to a Technicon autoanalyzer which makes it possible to fix the nutrient ($NO_2$ and $NO_3$) concentration conditions. The bioreactor is also coupled to a particle counter from HIAC (registered trademark), making it possible to monitor the production of biomass.

The pH of the culture medium is regulated during the working period by means of a generator of bubble curtains of air and $CO_2$ within the culture medium. The temperature of the culture medium is regulated by a thermostat which comprises the circulation of water at a setpoint temperature around the tank of the bioreactor. The light source comprises striplights and/or light filters, making it possible to illuminate at different light intensities. The supply of nutrients of the cell culture is controlled by dilution of the culture medium, which is dependent on the turbidity measurement. The nutrients required for the production of biomass may be added continuously or at a variable frequency.

The tank is mainly made of stainless steel with a volume of 1.9 liters. The tank has two walls made of plexiglas (interchangeable with polycarbonate walls). A first wall is arranged close to the light source, such that the light can penetrate within the tank in order to illuminate the cell culture. A second wall is arranged close to the light sensor, such that the latter can measure the output light intensity.

The light source comprises a striplight containing high-power light-emitting diodes (LEDs). The light source is capable of emitting light with a light intensity of 5000 µmol photons $m^{-2}$ $s^{-1}$.

The working period is 6 months. The cell culture consists of a wild-type strain of *Tisochrysis lutea* cells.

The cycles consist of periods of approximately 30 minutes at high intensity $I_{in1}$ (stress phases) followed by 90 minutes in darkness $I_{in0}$ (resting phase). The high light intensity $I_{in1}$ is 800 µmol photons $m^{-2}$ $s^{-1}$ at the start of the working period, then it has been increased in stages over the cycles up to 1600 µmol photons $m^{-2}$ $s^{-1}$. Table 1 below shows the details of each cycle:

TABLE 1 parameters of the selection cycles applied. $I_{in1}$: Light having an intensity set to the setpoint value; $I_{mean}$: Mean light intensity over one cycle; $t_{in1}$ = length of time per time slot [i.e. Period of irradiation at high light intensity (or second period of irradiation with an intensity set to the setpoint value)]; $t_{in0}$ = length of time per time slot at $I_{in0}$ [i.e. Resting period or period of irradiation at low light intensity (or first period of irradiation with an intensity set to the resting value)].

|  | $I_{in1}$ (µmol · $m^{-2}$ · $s^{-1}$) | $I_{mean}$ (µmol · $m^{-2}$ · $s^{-1}$) | $I_{in1} - I_{mean}$ (µmol · $m^{-2}$ · $s^{-1}$) | $t_{in1}$ (second) | $t_{in0}$ (second) | Number of time slots ($day^{-1}$) |
|---|---|---|---|---|---|---|
| Cycle 1 | 800 | 200 | 600 | 1800 | 3600 | 16 |
| Cycle 2 | 1000 | 300 | 700 | 2160 | 5040 | 12 |

TABLE 1-continued parameters of the selection cycles applied. $l_{in1}$: Light having an intensity set to the setpoint value; $l_{mean}$: Mean light intensity over one cycle; $t_{in1}$ = length of time per time slot [i.e. Period of irradiation at high light intensity (or second period of irradiation with an intensity set to the setpoint value)]; $t_{in0}$ = length of time per time slot at $l_{in0}$ [i.e. Resting period or period of irradiation at low light intensity (or first period of irradiation with an intensity set to the resting value)].

| | $l_{in1}$: ($\mu$mol·m$^{-2}$·s$^{-1}$) | $l_{mean}$ ($\mu$mol·m$^{-2}$·s$^{-1}$) | $l_{in1} - l_{mean}$ ($\mu$mol·m$^{-2}$·s$^{-1}$) | $t_{in1}$ (second) | $t_{in0}$ (second) | Number of time slots (day$^{-1}$) |
|---|---|---|---|---|---|---|
| Cycle 3 | 1200 | 350 | 850 | 2100 | 5100 | 12 |
| Cycle 4 | 1400 | 350 | 1050 | 1800 | 5400 | 12 |
| Cycle 5 | 1600 | 400 | 1200 | 1800 | 5400 | 12 |

Here, the difference $I_{in1}-I_{mean}$ is chosen so as to be at least greater than 400 $\mu$mol·m$^{-2}$·s$^{-1}$ or such that $I_{mean}$ is less than a third of $I_{in1}$.

Figure 4:
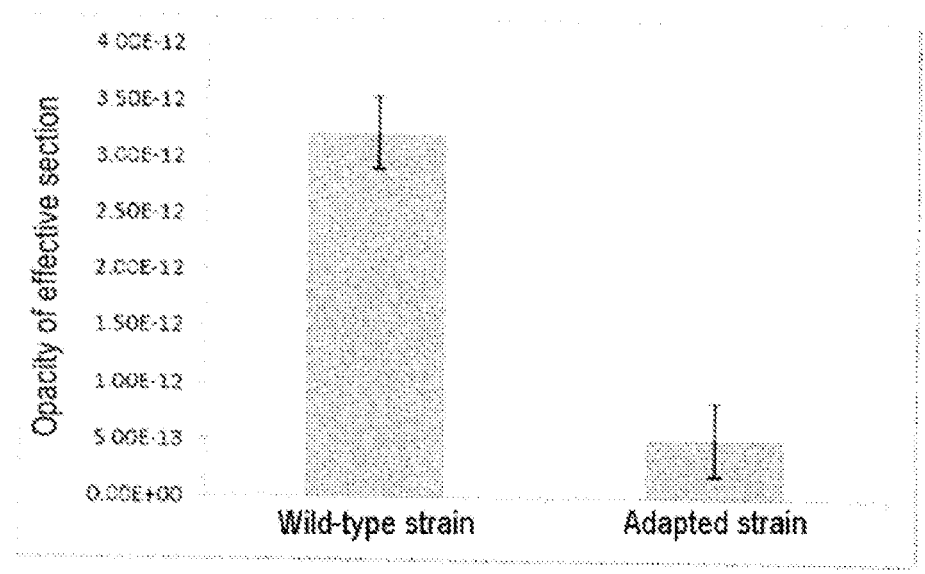
FIG. 4 shows a diagram featuring the opacity of a wild-type microalgal strain and the opacity of a strain selected by the bioreactor of the invention.

FIG. 4 shows the opacity of the wild-type strain of *Tisochrysis lutea* and the opacity of the strain of *Tisochrysis lutea* selected by the bioreactor of the invention after the working period. The strain selected has increased resistance to photoinhibition. This strain may be termed "adapted strain" since it results from genetic adaptation (point mutations) of the wild-type strain of *Tisochrysis lutea*.

The measurements of opacity (or of effective section) show that the cells of the adapted strain are more than six times more transparent than the wild-type strain. The effective section represents the total surface area of the light harvesting complexes. Decreasing this surface area equates to making the microalgae more transparent.

Figure 5:
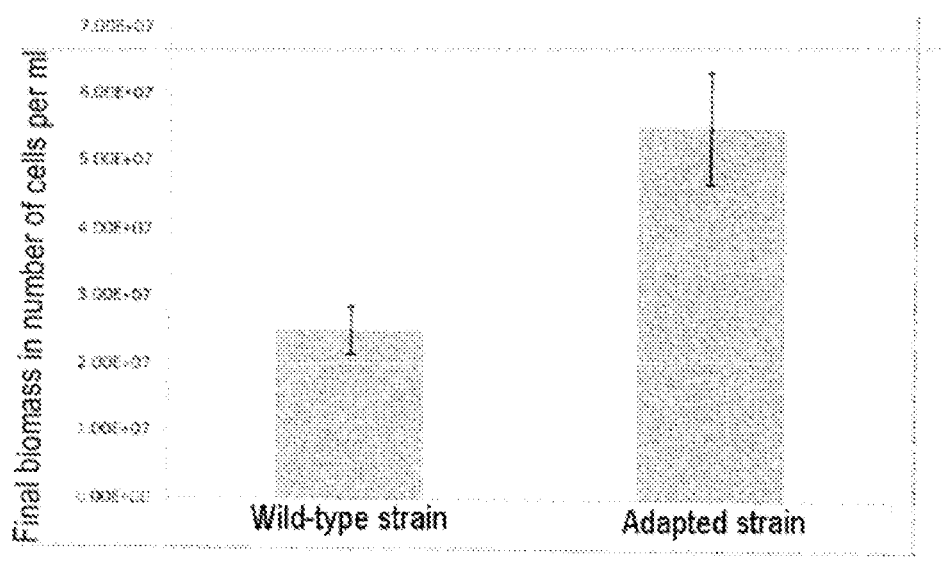
FIG. 5 shows the production of biomass of the wild-type strain and the selected strain from FIG. 4.

FIG. 5 shows the production of biomass of the wild-type strain and the production of biomass of the adapted strain in a conventional culture system of batch type with continuous light at a light intensity of 110 $\mu$mol photons m$^{-2}$ s$^{-1}$.

The production of biomass of the adapted strain is doubled compared to the production of biomass of the wild-type strain. The bioreactor of the invention is therefore of great benefit in the industrial production of microalgal biomass.

The biomass is produced conventionally in a cylindrical glass photobioreactor at a constant light intensity of 110 $\mu$mol photons m$^{-2}$ s$^{-1}$, at a constant temperature of 28° C. and at a constant pH of 8.2, in batch type control.

The invention also relates to the use of the bioreactor as defined above for the production of biomass of a cell culture chosen from the group consisting of the Chlorophyceae classes, such as *Chlamydomonas* sp., *Dunaliella salina* and *Haematococcus pluvialis*, Baciliariophyceae (Diatomophyceae) classes, such as *Phaeodactylum tricornutum* and *Odontella aurita*, Isochrysidaceae classes, such as *Isochrysis galbana* and *Tisochrysis lutea*, Trebouxiophyceae classes, such as *Chlorella vulgaris*, and Cyanophyceae classes, such as *Arthrospira platensis*.

The invention also relates to a process for selecting photosynthetic microorganisms. The process makes it possible to select strains of photosynthetic microorganisms having increased resistance to photoinhibition from a population of photosynthetic microorganisms (or cell culture of photosynthetic microorganisms). The strains selected may be used for the production of biomass. The industrial exploitation of the photosynthetic microorganisms selected affords good production yields. The process comprises the following steps:

1. providing a bioreactor comprising a light source, and a tank arranged facing the light source intended to receive a culture medium comprising a cell culture of photosynthetic microorganisms, said light source being capable of emitting a light with an input light intensity $I_{in}$ in the direction of the tank,
2. filling the tank with a culture medium;
3. inoculating the culture medium with a cell culture composed of photosynthetic microorganisms;
4. controlling the tank for a working period to a chosen cell culture concentration $x_i$ in the culture medium;
5. setting the input light intensity $I_{in}$ to a setpoint value enabling to induce cellular stress in at least some of said photosynthetic microorganisms;
6. keeping the input light intensity $I_{in}$ at the setpoint value for a period less than or equal to said working period, so as to cause cellular degradation of at least a portion of said photosynthetic microorganisms and thereby select the photosynthetic microorganisms having increased resistance to photoinhibition; and
7. harvesting the photosynthetic microorganisms having increased resistance to photoinhibition from said culture medium.

Cellular degradation is intended to mean any degradation resulting in the elimination of a cell from the culture medium. This may most particularly be cell death. Cell death may be caused by physical or chemical damage—this is cell necrosis; cell death may be caused by cell suicide—this is apoptosis. Moreover, this may be mitotic death (stopping cell division) in which the cell can no longer reproduce and ends up being evacuated from the bioreactor when the latter is continuously controlled.

The degradation of the cells sensitive to cellular stress results in the population of resistant cells (or cells that have become resistant by genetic mutation) increasing in the culture medium. Thus, the harvesting at step 7. is carried out when the culture medium comprises a cell culture of photosynthetic microorganisms consisting of more than 75%, preferentially of more than 90%, even more preferentially substantially of 100%, of microorganisms having increased resistance to photoinhibition.

Step 6. may comprise the following sub-steps:
6a. setting the light to an input light intensity), at a resting value lower than the setpoint value, for a period less than said working period;
6b. maintaining the input light intensity $I_{in}$ at the resting value for a period less than said working period; and
6c. successively switching between the resting value and setpoint value during the working period.

Of course, in this embodiment, in step 6., the input light intensity $I_{in}$ is maintained at the setpoint value for a period less than the working period. This is necessary in order to be able to switch between the resting value and the setpoint value throughout the whole of the working period.

Moreover, in this embodiment, the process may comprise the following sub-steps:
fixing a first irradiation period for which the light is set to an input light intensity $I_{in}$ at the resting value; and
fixing a second irradiation period for which the light is set to the setpoint value.

For reasons of photoacclimation, the first irradiation period is preferably greater than the second irradiation period. This embodiment therefore results in the succession of first irradiation periods and of second irradiation periods. Each first irradiation period, during which the light is set to the input light intensity $I_{in}$ at the resting value, is followed by a second irradiation period, during which the light is set to the input light intensity $I_{in}$ at the setpoint value. The microalgae cells are thus subjected to the succession of stress phases and of photoacclimation phases (or resting phases). It should be noted that the input light intensity $I_{in}$ at the resting value may correspond to the absence of light, namely to darkness; therefore 0 µmol quanta $m^{-2}$ $s^1$. In other embodiments the resting value may be between 10 and 200 µmol quanta $m^{-2}$ $s^{-1}$, for example 50 µmol quanta $m^{-2}$ $s^{-1}$ or 100 µmol quanta $m^{-2}$ $s^{-1}$.

Preferably, the first and second irradiation periods are fixed such that the mean value of the input light intensity $I_{in}$ during the working period, calculated from the resting value and the setpoint value, is less than or equal to a third of said setpoint value. This ensures sufficient resting time for the cells to be able to acclimatize to the stress conditions. In a particular embodiment, the first irradiation period is at least three times greater than the second irradiation period.

Preferably, the working period is greater than the time required for at least 20 cell cycles, preferably 100 cell cycles, of each initial microalgal cell present in the culture medium.

Advantageously, the process implements successive repetition of steps 5. and 6. until a cell culture of photosynthetic microorganisms substantially consisting of microorganisms having increased resistance to photoinhibition is obtained. The repetition of the steps enables satisfactory selection and promotes photoacclimation of the cells.

The process may also comprise the following steps:
8. inoculating a culture medium with the photosynthetic microorganisms harvested in step 7. in a bioreactor; and
9. controlling the bioreactor of step 8. for production of biomass formed of said photosynthetic microorganisms.

This step may be carried out in the same bioreactor or in a separate bioreactor particularly suited to the production of biomass. For example, the bioreactor may be a culture pond ("raceway" type pond) and a closed culture system such as batch bioreactors, fed batch bioreactors or continuous bioreactors.

The process of the invention may also comprise a sub-step 4a. comprising measuring the output light intensity $I_{out}$. The input light intensity $I_{in}$ at step 5. may then be set as a function of the output light intensity $I_{out}$ measured in step 4a. In this embodiment, the bioreactor comprises a light sensor arranged opposite said light source relative to the tank (the sensor is facing the light source). The light sensor is arranged so as to measure the output light intensity $I_{out}$.

Preferably, the setpoint value of the input light intensity $I_{in}$ is greater than or equal to 500 µmol quanta $m^{-2}$ $s^{-1}$. In a particular embodiment, the setpoint value is greater than or equal to 800 µmol quanta $m^{-2}$ $s^{-1}$.

In another particular embodiment, the setpoint value increases in stages over the working period (for example in stages of 200 µmol quanta $m^{-2}$ $s^{-1}$). This makes it possible to further increase selection. A stricter selection is therefore achieved. At the end of the working period, only the microalgae that are highly resistant to photoinhibition remain in the culture medium. The following setpoint values may especially be applied successively: 800 µmol quanta $m^{-2}$ $s^{-1}$; 1000 µmol quanta $m^{-2}$ $s^{-1}$; 1200 µmol quanta $m^{-2}$ $s^{-1}$; 1400 µmol quanta $m^{-2}$ $s^{-1}$; 1600 µmol quanta $m^{-2}$ $s^{-1}$. The phases during which the input light intensity $I_{in}$ is set to the setpoint values may optionally be followed by phases during which the input light intensity $I_{in}$ is set to the resting value, for example to a value close or equal to 0 µmol quanta $m^{-2}$ $s^{-1}$ (darkness) or close to 50 to 100 µmol quanta $m^{-2}$ $s^{-1}$. This enables the microalgae to acclimatize and, where appropriate, to begin modification on a molecular level (especially genetic mutations).

Preferably, the controlling in step 4. Is carried out at a concentration (for example at a value from 0.001 g/l to 10 g/l, preferably between 0.05 g/l and 0.1 g/l or between 0.1 g/l and 5 g/l).

The invention claimed is:
1. A bioreactor, characterized in that it comprises a light source, a light sensor facing said light source, a tank arranged between the light source and the light sensor intended to receive a culture medium comprising a cell culture of photosynthetic microorganisms, a controller connected to the light sensor to control the tank to a chosen cell culture concentration ($x_i$) in the culture medium during a working period, said light source arranged to emit an incident light (L) with an input light intensity ($I_{in}$) in the direction of the tank, and the light sensor arranged to measure an output light intensity ($I_{out}$) of light from the light source passing through the tank and to transmit data relating to the output light intensity ($I_{out}$) to the controller for controlling the tank, and a control system connected to the light source to control the light source, the control system configured to:
set, for a period less than said working period, the input light intensity ($I_{in}$) of the light from the light source to a setpoint value to induce cellular stress in at least some of said photosynthetic microorganisms,
set the input light intensity ($I_{in}$) of the light from the light source during the working period to a resting value lower than the setpoint value,
switch the input light intensity ($I_{in}$) of the light from the light source between the resting value and the setpoint value during the working period,
fix a first irradiation period for which the input light intensity ($I_{in}$) of the light from the light source is set to the resting value and a second irradiation period for which the input light intensity ($I_{in}$) of the light from the light source is set to the setpoint value, and
apply a succession of the first and second irradiation periods, the first irradiation period being greater than the second irradiation period and the first and second irradiation periods are fixed such that the mean value of the input light intensity ($I_{in}$) of the light from the light source during the working period, calculated from the resting value and the setpoint value, is less than or equal to a third of said setpoint value.
2. The bioreactor as claimed in claim 1, wherein the setpoint value is greater than or equal to 500 µmol quanta $m^{-2}$ $s^{-1}$.

3. The bioreactor as claimed in claim 2, wherein the setpoint value is greater than or equal to 800 µmol quanta $m^{-2} s^{-1}$.

4. The bioreactor as claimed in claim 1, wherein the chosen cell culture concentration ($x_i$) in the culture medium is between 0.001 g/l and 0.1 g/l.

5. The bioreactor as claimed in claim 4, wherein the chosen cell culture concentration ($x_i$) in the culture medium is between 0.05 g/l and 0.1 g/l.

6. The bioreactor as claimed in claim 1, wherein the first irradiation period is at least three times greater than the second irradiation period.

7. The bioreactor as claimed in claim 1, wherein the control system is also configured to fix a plurality of first and second irradiation periods during which the light is set to an input light intensity ($I_{in}$) at the resting value during each first irradiation period and the light is set to an input light intensity ($I_{in}$) at the setpoint value during each second irradiation period.

8. The bioreactor as claimed in claim 7, wherein the control system is also configured to fix the setpoint value at each second irradiation period.

9. The bioreactor as claimed in claim 1, wherein the chosen cell culture concentration ($x_i$) in the culture medium is between 0.1 g/l and 10 g/l.

10. The bioreactor as claimed in claim 9, wherein the chosen cell culture concentration ($x_i$) in the culture medium is between 1 g/l and 10 g/l.

11. The bioreactor as claimed in claim 9, wherein the control system is configured to maintain the input light intensity ($I_{in}$) at the setpoint value, such that the output light intensity ($I_{out}$) is substantially constant for a period less than or equal to the working period.

12. The bioreactor as claimed in claim 1, wherein the control system is connected to the light sensor to receive the data relating to the output light intensity and the control system is configured to control the light source based on the data relating to the output light intensity.

13. A process for selecting photosynthetic microorganisms, comprising the following steps:
 1. providing a bioreactor comprising a light source and a tank arranged facing the light source intended to receive a culture medium comprising a cell culture of photosynthetic microorganisms, said light source emitting a light with an input light intensity $I_{in}$ the direction of the tank;
 2. filling the tank with a culture medium;
 3. inoculating the culture medium with a cell culture composed of photosynthetic microorganisms;
 4. controlling the tank for a working period to a chosen cell culture concentration $x_i$ in the culture medium;
 5. setting, by a control system, the input light intensity to a setpoint value to induce cellular stress in at least some of said photosynthetic microorganisms;
 6. maintaining, by the control system, the input light intensity at the setpoint value for a period less than said working period, so as to cause cellular degradation of at least a portion of said photosynthetic microorganisms and thereby select the photosynthetic microorganisms having increased resistance to photoinhibition, wherein step 6 further includes:
    6a. setting, by the control system, the light to an input light intensity at a resting value lower than the setpoint value for a period less than said working period;
    6b. maintaining, by the control system, the input light intensity at the resting value for a period less than said working period; and
    6c. successively switching between the resting value and setpoint value during the working period by the control system;
 7. fixing, by the control system, a first irradiation period for which the light is set to an input light intensity at the resting value and a second irradiation period for which the light is set to the setpoint value such that the mean value of the input light intensity during the working period, calculated from the resting value and the setpoint value, is less than or equal to a third of said setpoint value; and
 8. harvesting the photosynthetic microorganisms having increased resistance to photoinhibition from said culture medium.

14. The process as claimed in claim 13, wherein the harvesting at step 8 is carried out when the culture medium comprises a cell culture of photosynthetic microorganisms consisting of more than 75% of microorganisms having increased resistance to photoinhibition.

15. The process as claimed in claim 13, also comprising the following steps:
 9. inoculating a culture medium with the photosynthetic microorganisms harvested in step in a bioreactor; and
 10. controlling the bioreactor of step 9 for production of biomass formed of said photosynthetic microorganisms.

16. The process as claimed in claim 13, wherein the bioreactor also comprises a light sensor opposite said light source relative to the tank, the process also comprising:
 4a. measuring the output light intensity ($I_{out}$) of light from the light source passing through the tank with the light sensor; and
 wherein the input light intensity ($I_{in}$) at step 5 is set as a function of the output light intensity ($I_{out}$) measured in step 4a.

17. The process as claimed in claim 13, wherein the harvesting at step 8 is carried out when the culture medium comprises a cell culture of photosynthetic microorganisms consisting of more than 90% of microorganisms having increased resistance to photoinhibition.

18. The process as claimed in claim 13, wherein the harvesting at step 8 is carried out when the culture medium comprises a cell culture of photosynthetic microorganisms consisting of substantially 100% of microorganisms having increased resistance to photoinhibition.

* * * * *